United States Patent
Pierron et al.

(10) Patent No.: US 11,610,647 B2
(45) Date of Patent: Mar. 21, 2023

(54) METHOD AND SYSTEM FOR GENERATING A UNIQUE IDENTIFIER OF A SUBJECT FROM THE DNA OF SAID SUBJECT

(71) Applicants: CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); UNIVERSITE PAUL SABATIER TOULOUSE III, Toulouse (FR)

(72) Inventors: Denis Pierron, Toulouse (FR); Thierry Letellier, Le Bouscat (FR); Margit Heiske, Toulouse (FR); Veronica Pereda, Portet sur Garonne (FR)

(73) Assignees: CENTRE NATIONAL DE LA RECHERCHE SCIENTIFIQUE (CNRS), Paris (FR); INSTITUT NATIONAL DE LA SANTE ET DE LA RECHERCHE MEDICALE, Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 447 days.

(21) Appl. No.: 16/756,775

(22) PCT Filed: Oct. 18, 2018

(86) PCT No.: PCT/EP2018/078517
§ 371 (c)(1),
(2) Date: Apr. 16, 2020

(87) PCT Pub. No.: WO2019/077025
PCT Pub. Date: Apr. 25, 2019

(65) Prior Publication Data
US 2021/0193256 A1 Jun. 24, 2021

(30) Foreign Application Priority Data

Oct. 18, 2017 (FR) ...................................... 1759779

(51) Int. Cl.
*G16B 20/20* (2019.01)
*G16B 40/00* (2019.01)

(52) U.S. Cl.
CPC ............. *G16B 20/20* (2019.02); *G16B 40/00* (2019.02)

(58) Field of Classification Search
CPC ......... G16B 20/00; G16B 20/20; G16B 40/00
See application file for complete search history.

(56) References Cited

U.S. PATENT DOCUMENTS

| 5,856,104 A * | 1/1999 | Chee .................... C12Q 1/6876 536/24.31 |
| 2004/0267458 A1* | 12/2004 | Judson ................... G16B 20/40 702/20 |

(Continued)

FOREIGN PATENT DOCUMENTS

WO    WO-0106454 A1 *  1/2001   ............. G16B 30/00

OTHER PUBLICATIONS

Zeng et al., "Evaluation of 96 SNPs in 14 Populations for Worldwide Individual Identification", Journal of Forensic Sciences, Jul. 2012, vol. 57, No. 4, pp. 1031-1035 (Year: 2012).*

(Continued)

*Primary Examiner* — Nay A Maung
*Assistant Examiner* — Jose M Torres
(74) *Attorney, Agent, or Firm* — Maier & Maier, PLLC

(57) ABSTRACT

The invention relates to a method for generating a unique identifier of a subject from a genotyped DNA sample from said subject, the method comprising the steps of: obtaining a number N≥2 of genomic positions of interest, said obtained genomic positions being such that, in a population (Continued)

of M subjects, these genomic positions exhibit a polymorphism of at least one nucleotide having an allelic frequency of between 25% and 35%, for the minority allele; combining in pairs the obtained genomic positions by means of logical functions so as to obtain a binary code bc.

11 Claims, 2 Drawing Sheets

(56) References Cited

U.S. PATENT DOCUMENTS

2014/0243229 A1* 8/2014 Landers ............... C12Q 1/6827
506/9
2018/0322956 A1* 11/2018 Constantine ........... G16H 50/20

OTHER PUBLICATIONS

LaRue et al., "Characterization of 114 insertion/deletion (INDEL) polymorphisms, and selection for a global INDEL panel for human identification", Legal Medicine 16, 2014, pp. 26-32 (Year: 2014).*

Goodin et al., "Singe Nucleotide Polymorphism (SNP)—Strings: An Alternative Method for Assessing Genetic Associations", PLoS One, 2014; 9(4): e90034, pp. 1-20 (Year: 2014).*

* cited by examiner

METHOD AND SYSTEM FOR GENERATING A UNIQUE IDENTIFIER OF A SUBJECT FROM THE DNA OF SAID SUBJECT

GENERAL TECHNICAL FIELD

The invention relates to the field of biometric authentication and more particularly relates to the generation of a unique identifier of a subject from said subject's DNA.

RELATED ART

The stakes linked to the concept of identity are high and cover very broad areas, ranging from administrative needs (nationality, voting rights, health, pensions, etc.) to national security requirements (borders, crime, victims, missing persons) and the protection of property and data (banking, medical information, etc.). These issues imply a guarantee as to the identity of individuals.

The use of the biometric traits of individuals is therefore of interest.

To authenticate individuals, several methods based on one or more biometric traits have been implemented.

In India, for example, a population identification system has been set up which allows a national identification number to be assigned to each individual based on fingerprints or a photograph of the iris.

There are also known voting systems that use fingerprint recognition to identify voters.

However, the use of these biometric features is not without problems:
- Identification by these traits is no longer possible if the biometric trait observed is altered (aging, cosmetic surgery, accident);
- These traits are often altered during childhood, so it is difficult to identify an adolescent/adult from traits measured at birth or early childhood;
- Measurements of these traits may not be completely reliable;
- The holder of the biometric feature may be put at risk if an attempt is made to misuse the biometric feature;
- It is not possible to change the identifier.

DISCLOSURE OF THE INVENTION

The invention proposes to overcome at least one of these drawbacks by providing a means of identifying individuals in a powerful and unique way while guaranteeing both the security and the privacy of individuals.

For this purpose, the invention provides a process for generating a unique identifier of a subject from a genotyped DNA sample of said subject, the process comprising the steps of:
- obtaining a number of genomic positions of interest, said genomic positions obtained being such that in a population of M subjects, these genomic positions have a polymorphism of at least one nucleotide having an allelic frequency of between 25% and 35%, for the minority allele;
- combining pairwise the genomic positions obtained by means of logic functions so as to obtain a binary code bc.

The invention is advantageously complemented by the following features, taken alone or in any technically possible combination thereof:
- the allelic frequency is 29%;
- the polymorphism is a single-nucleotide polymorphism (SNP);
- the polymorphism is binary;
- the pairwise-combined positions are not linked and are preferentially at least 100 centimorgans or on different chromosomes;
- the polymorphism is an insertion or deletion of at least two nucleotides;
- the polymorphism is binary;
- the combination consists in comparing the genomic positions of interest in the following way: the positions obtained are $P_i$, i=1 to N; logical states '1' or '0' are assigned as follows: $P_i$='1' if on the two variations of the $SNP_i$ at least one allele 1 is present, otherwise $S_i$='0'; logical pairwise combination of $P_i$ to obtain the binary code bc;
- the positions obtained are non-coding for the subject and at least do not include information on the sex of the subject;
- the process comprises a step of encrypting the binary code obtained, the encrypted code being also binary;
- the process comprises a step of converting the binary code obtained into a hexadecimal code or QR code.

The invention relates to a system for generating a unique identifier of a subject from a genotyped DNA sample of said subject, comprising a processor configured to implement a process according to the invention.

The advantages of the invention are manifold.

The invention is based on DNA that is available identically in any part of the human body (except for somatic mutations).

The generated identifier is unique for each individual, anonymous, stable over time, in particular it does not deteriorate and is forgery-proof. Moreover, the storage of the identifier is simple because it does not require a lot of space as opposed to a raw storage of an individual's genetic information.

The invention thus makes it possible to generate a unique identifier for each subject (with the exception of identical twins or clones). This identifier is based on the genetic diversity of the species studied throughout the world. Knowledge of this diversity makes it possible to specifically choose genomic positions and to mathematically calculate the probability that subjects possess the same identifier. It is thus possible to demonstrate that around 100 appropriately chosen positions will be sufficient to make this probability nil. The method proposed here is based on the notion of position pair. In fact, using two positions (i.e. a position pair), the probability that two subjects taken at random share the same code is ½. The corresponding general formula is $0.5^n$ with n being the number of position pairs studied. Thus 100 studied positions correspond to 50 pairs, i.e. a probability of $0.5^{50}$ or $10^{-15}$.

The identifier itself is anonymous in that it is impossible to obtain any information about the person (age, place of birth, sex, region of origin, physical characteristics, genomic characteristics). In other words, a person's identifier does not provide any information that could potentially help characterize him or her in any way. Because of its design and the characteristics of genetic markers, it is impossible to obtain information from the genome used to generate the identifier, even for the holders of the algorithm that was used to generate the identifier.

The invention makes it possible to obtain a fundamentally different identifier between two subjects, whether they are taken at random or belong to the same family. The fact of belonging to the same population has no influence on the identifier. For example, for two identifiers composed of 20 hexadecimal digits, the probability of two subjects sharing the same identifier is less than 1 chance in 72 quadrillion.

The DNA analysis of an individual will always give the same forgery-proof and timeless identifier. The identifier is therefore timeless. Thus, from birth to death, an individual will always have the same genome (and de facto the same identifier). Since DNA is preserved well postmortem, it is possible to verify an individual's identifier long after death (it is even possible to generate the identifier of an individual who has been dead for 40 000 years).

Advantageously, the final identifier is a hexadecimal code that can be easily read and allows instant identification with computer means by comparing it to a register of several million or even billions of numbers.

The applications of the invention are manifold.

It is possible to use the same methodology outlined here to create different types of identifiers (one specific identifier for legal applications, another for banking applications, etc.) for a subject (by changing the positions chosen, for example).

The identifier makes it possible to respond to problems of authentication and banking secrecy, the invention making it possible to generate independent identifiers for each application.

This identifier can be used by forensics to identify an individual.

This identifier makes it possible, for example, to open a bank account. Thus, only the person whose genome corresponds to the identifier can access the contents of the account.

This identifier makes it possible, for example, to open an account to store personal papers (properties, identifications) or money for oneself or one's children with a guarantee that the beneficiary will be able to access it in the future. This is particularly useful in the event of a catastrophic event when identification papers or other usual means of identification are lost (flood, fire, war, sudden death of both parents, etc.).

The examples given above are by no means exhaustive, other applications using identification may implement the identifier of the invention.

PRESENTATION OF THE FIGURES

Other features, purposes and advantages of the invention will be apparent from the following description, which is purely illustrative and non-limiting, and which should be read in conjunction with the appended drawings wherein.

DETAILED DESCRIPTION OF THE INVENTION

Figure 1:
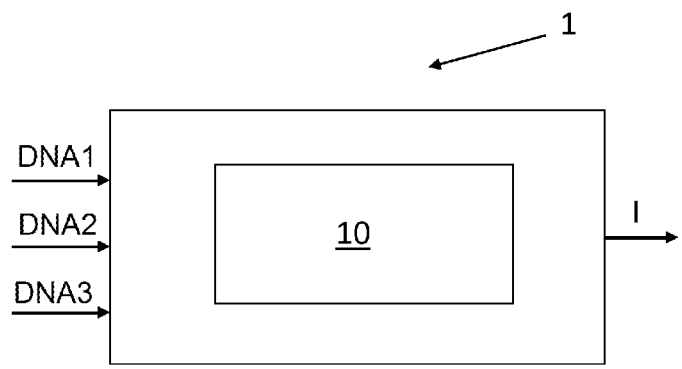
FIG. 1 illustrates a system for generating an identifier according to an embodiment of the invention.
Figure 2:
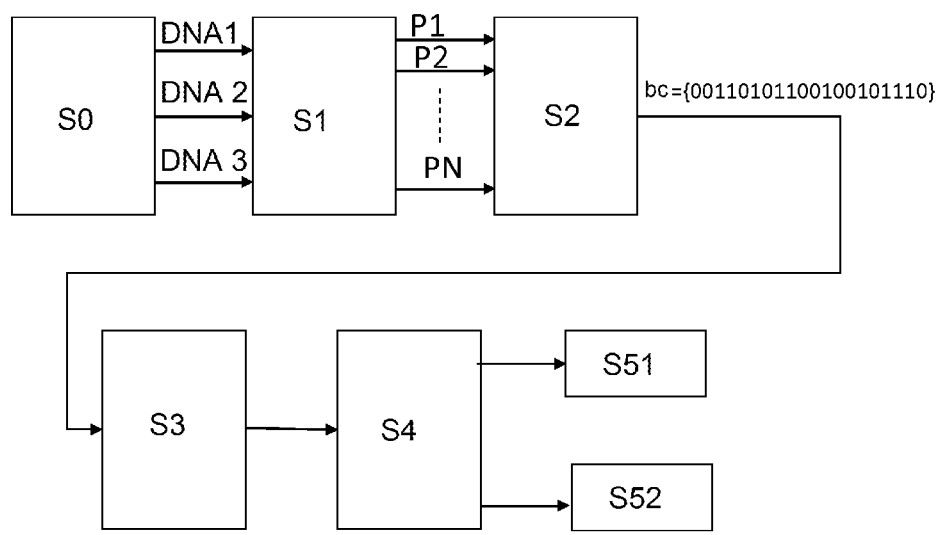
FIG. 2 illustrates a process for generating an identifier according to an embodiment of the invention.

In connection with FIG. 1 a system 1 for generating an identifier of a subject from a DNA sample of said subject comprises a processing unit 10 (for example a processor) configured to implement a process for generating an identifier from a DNA sample described below in connection with FIG. 2.

The subject or individual can be any entity composed of DNA (a human being, an animal, a plant, etc.).

In a preliminary step (step S0), at least one sample of DNA1, DNA2, DNA3 is taken from a subject. Preferably, samples are taken from several different locations (for example three different locations). The sample is, for example, saliva, blood, hair, etc. or more generally anything that allows many types of biological samples containing cells from the individual to be taken.

From the samples taken, the subject's DNA is sequenced/genotyped (step S1).

The sequencing/genotyping makes it possible to obtain genomic positions of interest (step S2) $P_i$, i=1, ..., N.

Genotyping may or may not target positions of interest and can be generated by multiple procedures (microarrays, sequencing or other). Thus, the procedure described here can be used both from the results of custom-generated microarrays and from a complete sequencing of the individual's genome (only the positions of interest will be kept). The number of positions used depends on the desired level of uniqueness and security according to the formula presented above. In other words, steps S1 and S2 can be implemented simultaneously.

The total number of positions studied can typically be 100.

The genomic positions of interest are not arbitrary but are such that considering M subjects (the subject for which the code is generated may or may not belong to these M subjects) these positions present a polymorphism of at least one nucleotide with an allelic frequency between 25% and 35% in the population. In addition, these positions respect Hardy-Weinberg equilibrium and the position is not located on a sex chromosome or on mtDNA.

Specifically, the ideal allelic frequency of polymorphism is 29%.

The polymorphism considered in the M subjects can, in the simplest way, be a single-nucleotide polymorphism (SNP). Alternatively, the polymorphism considered on the M subjects can concern two nucleotides but it can also be a question of nucleotide insertion or deletion (INDEL).

Of course, the simplest polymorphism is t a single-nucleotide polymorphism.

Preferably, the polymorphism considered is binary in that the differences considered are only between two different alleles of a position. Thus, one allele is considered to have a '1' state and one allele is considered to have a '0' state. This convention facilitates the subsequent stages of the process.

Preferably, but not restrictively, the positions studied are not located on a coding part (gene) of the genome.

These sequences will be discussed later.

The polymorphisms obtained are then combined together, pairwise, by means of logic functions to obtain a binary code bc (step S3).

In the case introduced, of a binary polymorphism, the combination consists in comparing the positions in the following way:
   the positions obtained are $S_i$, i=1 to N;
   logic states '1' or '0' are assigned as follows: $S_i$='1' if on both SNPi variations at least one allele 1 is present, otherwise $S_i$='0'.
   the $P_i$'s are combined pairwise to get the binary code bc.
   Each element of the binary code corresponds to a combination of two sequences.
   The combination is implemented by means of a logic function.
   A logical function is for example: Exclusive OR (XOR), Or (OR), AND (AND), NEITHER ... NOR (NOR), NOT BOTH (NAND) ....

Of course, the logic function can be a more or less complex combination of these elementary logic functions.

Alternatively and more generally, the combination can obey any type of function in order to have a maximum of possible combinations.

Irrespective of the combinatorial logic chosen, it is necessary to have combinations of positions whose genotype can be considered independent, i.e. they will not be in linkage disequilibrium. To avoid this possibility, positions should be chosen that are physically distant from each other, i.e. ideally on different chromosomes or more than 100 centimorgans apart if they are located on the same chromosome (knowing that a distance of 50 centimorgans represents a 50% probability of recombination between two positions in one generation).

Once this binary code is obtained, it can be encrypted (step S4) but it is not mandatory. The encryption of the binary code protects the obtained binary code.

Additionally, the encrypted or unencrypted binary code is converted into a hexadecimal code (step S51) or a QR code (step S52). Indeed, a hexadecimal code (i.e. a sequence of about 20 hexadecimal characters that can be directly translated from the binary using a reference table) is easier to store in a memory for example and to read. Similarly, a graphical form of this code, such as a barcode or QR code, can be produced for automated optical reading.

As indicated, the positions of interest in the genome are those which, in a population of M subjects, present an allelic frequency polymorphism of between 25% and 35%.

In the case of human beings, the subjects come from many countries on all continents, a position will only be of interest if the allelic frequency is homogeneous and remains between 25% and 35% in all populations. A polymorphism that would be absent in one population or 100% in another would be excluded. In the same way, all positions associated with an ethnic or geographical origin of the individual are excluded.

Positions are said to be of interest if the frequencies respect the predictions of Hardy-Weinberg models (this is the case for the vast majority of polymorphisms). According to this model, the frequency mentioned corresponds to positions whose polymorphism is present in 50% of the subjects.

Concretely, let us consider a polymorphic locus X of DNA with an allelic frequency of 29% which has 2 alleles: 1 and 0, so in a population, individuals can be homozygous (11 or 00) or heterozygous (10 and 01) for this locus. We can classify the individuals according to two states A or B:

state A represents being homozygous for the majority allele (11)

state B represents being homozygous for the minority allele (00) or being heterozygous (10 and 01)

We define as "common" the polymorphisms for which the two states (A and B) are equiprobable. That is to say that an individual has the same probability of being A or B (i.e. 50% each).

Figure 3:
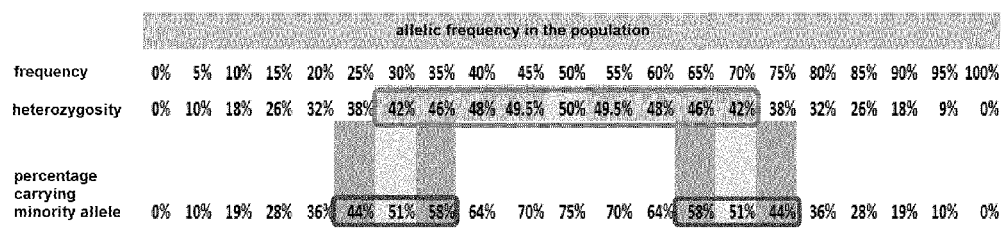
FIG. 3 illustrates data on sequences implemented in the invention.

FIG. 3 illustrates the relationships between allele frequencies, heterozygosity rates and minority allele carrier percentages. In this figure, several sequence information is reported (obtained according to Hardy-Weinberg principles): the first line indicates the allelic frequency in the population of M subjects, the second line indicates the percentage of heterozygosity, the third line indicates the percentage of carrier of the minority allele. We can see that for positions with an allelic frequency between 25% and 35%, we have between 44% and 58% of carriers of the allele considered (i.e. about one person in two) so that there is almost equiprobability that two individuals carry this sequence. Thus, given the number of data, and the fact that the codes are obtained by means of several sequences, the uniqueness of the code for a subject is guaranteed.

In addition to these frequency characteristics the positions must meet additional criteria: as mentioned above, the positions must not be located on sex chromosomes or on the mitochondrial chromosome. In addition, preference will be given to positions which are not located on coding areas of the genome and which are not associated with physical or behavioral characteristics or associated with a predisposition to certain diseases. The association of these positions is remarkable in that it allows identification of subjects without giving information on the subject.

The selection criteria can be summarized as follows.

Criterion 1: These polymorphisms have a worldwide frequency of homozygotes carrying the minority allele of 50% (±10%) which is equivalent to an allelic frequency of 29% (±7%).

Criterion 2: In order for an individual to have an identical probability of being A or B, the frequency of polymorphism must not vary greatly across human populations. Therefore, not only must the global frequency of the minority allele of polymorphism be 29% (±7%), but this frequency must not vary by more than 10% between 2 populations.

Criterion 3: The characteristics of the individual itself (gender or other physical characteristics, etc.) cannot be related to its probability of being A or B. Thus, common polymorphisms located only on autosomal chromosomes (and not on sex chromosomes) must not be related to known phenotypes or pathologies.

By way of example, below is a list of SNPs on chromosome 14 satisfying these characteristics:

| snp | chromosome | position |
| --- | --- | --- |
| rs111063713 | 14 | 104698456 |
| rs2416015 | 14 | 47511528 |
| rs4991272 | 14 | 59973009 |
| rs3985117 | 14 | 47511530 |
| rs7154083 | 14 | 83441172 |
| rs1686571 | 14 | 20279151 |
| rs57101715 | 14 | 90785895 |
| rs55795050 | 14 | 90782024 |
| rs8023212 | 14 | 90777846 |
| rs11845387 | 14 | 90785495 |
| rs574386930 | 14 | 96967163 |
| rs2792111 | 14 | 20418489 |
| rs148942138 | 14 | 79600280 |
| rs3742666 | 14 | 90767860 |
| rs118058626 | 14 | 39256730 |
| rs551716374 | 14 | 44995118 |
| rs4988990 | 14 | 101296722 |
| rs2635566 | 14 | 20418538 |
| rs67963498 | 14 | 41329594 |
| rs4902256 | 14 | 64406065 |

The invention claimed is:

1. A process for generating a unique identifier (I) of a subject from a genotyped DNA sample of said subject, the process comprising the steps of:

obtaining (S2) a number N≥2 of genomic positions of interest, said genomic positions obtained being such that, in a population of M subjects, these genomic positions have a polymorphism of at least one nucleotide having an allelic frequency of between 25% and 35% for the minority allele;

combining (S3) pairwise the genomic positions obtained by means of logic functions so as to obtain a binary code bc.

2. The process as claimed in claim 1, wherein the allelic frequency is 29%.

3. The process as claimed in claim 1, wherein the polymorphism is a single-nucleotide polymorphism (SNP).

4. The process as claimed in claim 1, wherein the polymorphism is binary.

5. The process as claimed in claim 4, wherein the polymorphism is a single-nucleotide polymorphism (SNP) and for an SNP of interest (SNPi) the combination compares genomic positions of interest as follows:
   the positions obtained are Pi, i=1 to N;
   logic states '1' or '0' are assigned as follows: Si='1' if on both variations of the SNPi at least one allele 1 is present, otherwise Si='0';
   logical pairwise combination of the logical states assigned to Pi to obtain the binary code bc.

6. The process as claimed in claim 1, wherein the pairwise-combined positions are not linked and are preferably at least 100 centimorgans apart or on different chromosomes.

7. The process as claimed in claim 1, wherein polymorphism is an insertion or deletion of at least two nucleotides.

8. The process as claimed in claim 1, wherein the positions obtained are non-coding for the subject and at least do not include information on the sex of said subject.

9. The process as claimed in claim 1, comprising a step (S4) of encrypting the binary code obtained, the encrypted code also being binary.

10. The process as claimed in claim 1, comprising a step of converting (S51, S52) the binary code obtained into a hexadecimal code or QR code.

11. A system for generating a unique identifier (I) of a subject from a genotyped DNA sample of said subject, comprising a processor configured to implement a process as claimed in claim 1.

* * * * *